(12) United States Patent
Fein et al.

(10) Patent No.: US 10,952,934 B1
(45) Date of Patent: Mar. 23, 2021

(54) DISPOSABLE WIPE AND METHODS OF USE THEREOF

(71) Applicant: Bunch of Jerks, LLC, Las Vegas, NV (US)

(72) Inventors: Samuel Ely Fein, Franklin, TN (US); Darrin Joseph Cohen, Pleasant Hill, CA (US)

( * ) Notice: Subject to any disclaimer, the term of this patent is extended or adjusted under 35 U.S.C. 154(b) by 0 days.

(21) Appl. No.: 16/883,745

(22) Filed: May 26, 2020

(51) Int. Cl.
*A61K 8/02* (2006.01)
*A61F 6/00* (2006.01)
*A61Q 19/10* (2006.01)
*A47K 7/03* (2006.01)

(52) U.S. Cl.
CPC .............. *A61K 8/0208* (2013.01); *A47K 7/03* (2013.01); *A61F 6/00* (2013.01); *A61Q 19/10* (2013.01)

(58) Field of Classification Search
CPC .... A61F 6/00; A61F 6/005; A61F 6/02; A61F 6/04; A61K 8/02; A61K 8/0208; A61K 8/361; A61K 8/41; A61K 8/42; A61K 8/67; A61K 8/678; A61K 8/92; A61K 8/922; B65D 81/24; B65D 75/30; B65D 85/62; B65D 85/00; A47K 7/03; A61Q 9/02; A61Q 19/10; C11D 1/662; C11D 3/22; C11D 17/00; C11D 17/003; C11D 17/04
USPC .................................. 128/844; 206/69, 438
See application file for complete search history.

(56) References Cited

U.S. PATENT DOCUMENTS

| | | | | | |
|---|---|---|---|---|---|
| 4,419,403 | A | * | 12/1983 | Varona | D21H 17/14 442/153 |
| 6,581,775 | B1 | * | 6/2003 | Hagopian | A61K 9/0034 206/69 |
| 7,204,368 | B2 | * | 4/2007 | Cheaure | B65D 31/12 206/440 |
| 9,427,383 | B2 | * | 8/2016 | McCauley | A61K 8/0208 |
| 2003/0106812 | A1 | * | 6/2003 | Wilkman | B65D 75/30 206/210 |
| 2012/0247981 | A1 | * | 10/2012 | Smith | A61F 6/005 206/69 |

FOREIGN PATENT DOCUMENTS

| | | | | |
|---|---|---|---|---|
| ES | 1072711 U | | 8/2010 | |
| GB | 2285428 A | * | 7/1995 | ............ A61F 6/005 |
| GB | 2299101 A | * | 9/1996 | ............ A61F 6/005 |
| GB | 2326867 A | * | 1/1999 | ............ A61F 6/005 |
| GB | 2420714 A | * | 6/2006 | ............ A61F 6/005 |
| WO | 2016082037 A1 | | 6/2016 | |

OTHER PUBLICATIONS

KR2008003527U Figure (Year: 2008).*
KR2008003527U Text (Year: 2008).*

* cited by examiner

*Primary Examiner* — Bryon P Gehman
(74) *Attorney, Agent, or Firm* — Bradley Arant Boult Cummings LLP; Timothy L. Capria

(57) ABSTRACT

A wipe comprising a flexible body is disclosed herewith. The wipe may be provided as a component of a wipe and a bag kit having the wipe and a bag, the wipe disposed within the bag. The wipe comprises a flexible body having an open end. The flexible body may be constructed of fabric. The wipe can be shaped and dimensioned complementary to a human male penis such that the human male penis may be inserted into the open end. The wipe may be pre-wetted with water and one or more additives.

22 Claims, 8 Drawing Sheets

US 10,952,934 B1

DISPOSABLE WIPE AND METHODS OF USE THEREOF

TECHNICAL FIELD

The present disclosure relates to a wipe, a kit of a wipe and a bag, and methods of use thereof. More specifically, the disclosure is directed towards personal hygienic wipes, kits, and methods of removing a condom.

BACKGROUND OF INVENTION

It is estimated that in the U.S. alone, about 450 million condoms are sold yearly. However, despite this extremely large quantity of condoms being consumed, bodily cleanup and disposal of condoms after their use remains problematic. Indeed, due to their single-use nature, typically condoms are packaged individually in a wrapper, with the wrapper being dimensioned only slightly larger than the unused condom. Thus, once a condom is used, it must be removed, along with the separate wrapper, be disposed of.

Meanwhile, disposal of used condoms presents hygienic and social challenges due to its intimate nature and because it contains bodily fluid (specifically, at the least, male ejaculate). For example, many people flush the used condom the toilet (despite condoms typically not being flushable and contrary to instructions for the condom). While common recommendations are to wrap the used condom in a newspaper or facial tissue, such items are often not available or easily accessible.

Moreover, cleaning the penis after removal of the condom remains an issue. Because the used condom contains ejaculate, when a condom is simply removed and flushed down a toilet or wrapped in a newspaper or facial tissue, ejaculate remains on the penis. Thus, for hygienic purposes, the penis must be washed or wiped down, creating more impracticalities for many sexual encounters.

Thus, a need exists for better apparatus and methods for disposing of a used condom and cleaning a penis after removing a condom.

BRIEF SUMMARY

In one aspect, a wipe and a bag kit is disclosed. The wipe and bag kit comprises a bag. The bag has a sealed state and an open state. The wipe and bag kit may comprise one or more wipes. The one or more wipes may be a single wipe. The one or more wipes comprise a flexible body. The flexible body may be generally cylindrical in shape and comprise an open end. The flexible body may be shaped complementary an erect or flaccid human penis such that the flexible body can cooperatively receive, at least partially, the penis through the open end. The flexible body may be constructed of fabric and may be multi-layer. The flexible body may comprise one or more open corners disposed at the open end, such as a first open corner and a second open corner disposed oppositely around the open end from the first open corner.

The wipe may comprise a composition. The composition may include a cleaning agent for cleaning skin of a human subject. The one or more wipes are disposed in the bag when the bag is in the sealed state.

In another aspect, a wipe is disclosed. The wipe comprises a flexible and generally cylindrical flexible body, an open end disposed on the flexible body, and one or more open corners disposed at the open end of the body. The one or more open corners may comprise a first open corner and a second open corner disposed oppositely around the open end from the first open. The flexible body may be constructed of a fabric and may comprise two or more layers. The wipe may further comprise an additive selected from the group consisting of a preservative, a lubricant, a cleaner, a fragrance, an emulsifier, a whitener, a skin softener, aloe, vitamin E, and combinations thereof. The wipe may be pre-wetted with a composition that contains at least 90% water by weight. The composition may comprise the additive. The wipe may be hypoallergenic, such as latex-free.

In yet another embodiment, a method of cleaning a human penis wearing a condom is disclosed. The method includes providing a wipe including a water-based cleaning agent and an open end, the wipe shaped to cooperatively receive the human penis wearing the condom through the open end. The method includes inserting the human penis through the open end at least partially within the wipe. The method includes removing the wipe and the condom together from the penis.

The wipe may be disposed within a sealed bag including a sealed state and an open state. The sealed bag may be resealable. The method may include, before the inserting, opening the sealed bag from a sealed state to an open state. The method may include, before the inserting, removing the wipe from the sealed bag in the open state. The method may include, after the removing, placing the removed wipe and the removed condom within the sealed bag in the open state. The method may include resealing the sealed bag having the removed wipe and removed condom disposed therein.

BRIEF DESCRIPTION OF DRAWINGS

It should be noted that identical features in different drawings are shown with the same reference numeral.

DETAILED DESCRIPTION

Figure 1:
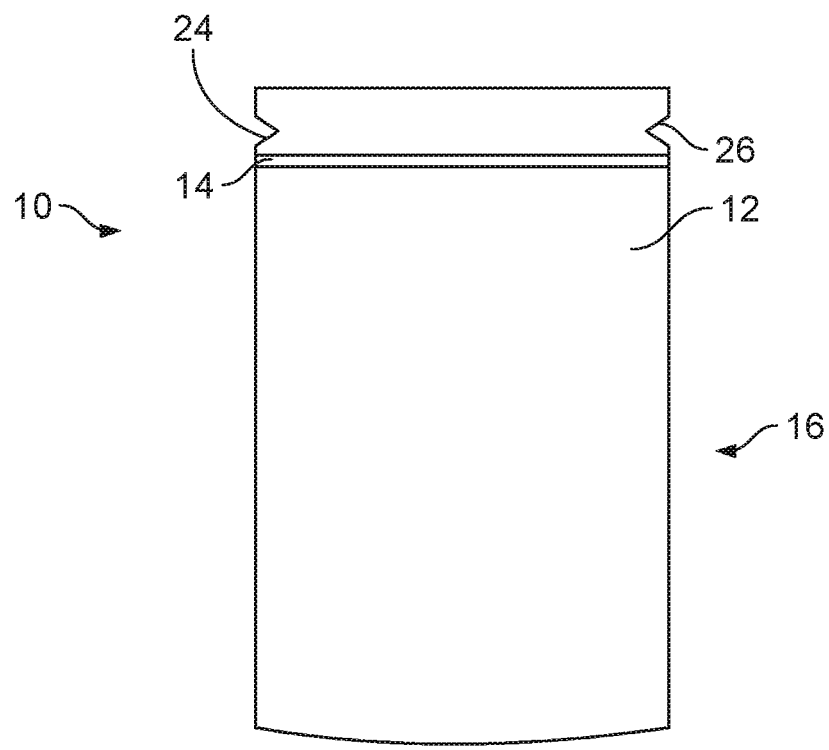
FIG. 1 shows a front elevation view of a wipe and bag kit with a wipe being in a bag when the bag is in a sealed state.
Figure 2:
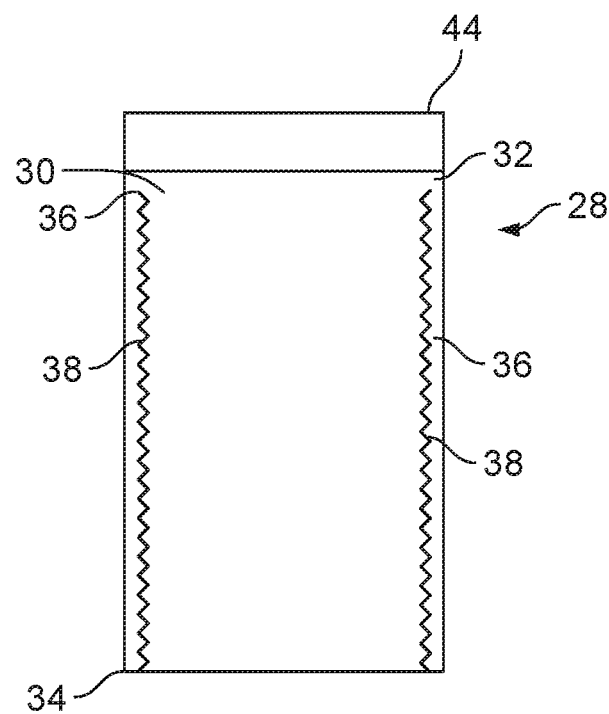
FIG. 2 shows a front elevation view of a wipe.
Figure 3:
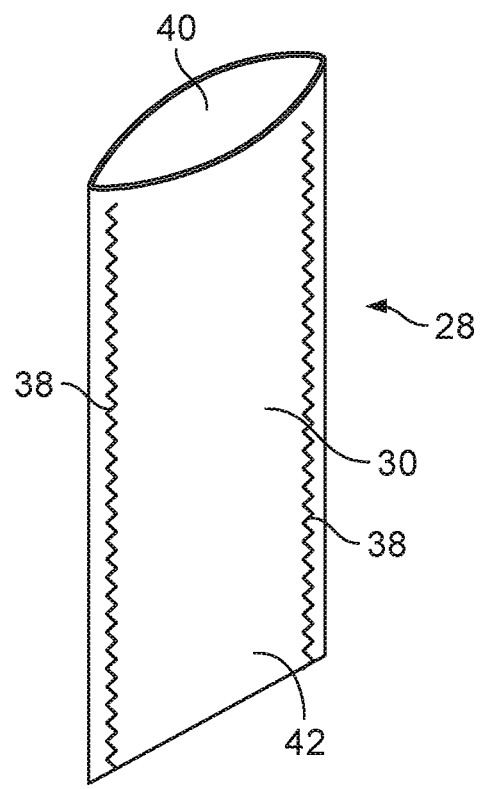
FIG. 3 shows a front perspective view of the wipe of FIG. 2.

Reference now will be made in detail to the embodiments of the present disclosure. It will be apparent to those of ordinary skill in the art that various modifications and variations can be made to the teachings of the present disclosure without departing from the scope of the disclosure. For instance, features illustrated or described as part of one embodiment can be used with another embodiment to yield a further embodiment.

Thus, it is intended that the present disclosure covers such modifications and variations that come within the scope of the appended claims and their equivalents. Other objects, features, and aspects of the present disclosure are disclosed in or are apparent from the following description. It is to be understood by one of ordinary skill in the art that the present disclosure is a description of exemplary embodiments only and is not intended as limiting the broader aspects of the present disclosure.

For the sake of clarity, not all reference numerals are necessarily present in each drawing Figure. In addition, positional terms such as "upper," "lower," "side," "top," "bottom," "vertical," "horizontal," etc. refer to the wipe or bag when in the orientation shown in the drawings. The skilled artisan will recognize that the wipe or bag can assume different orientations when in use.

Figure 6:
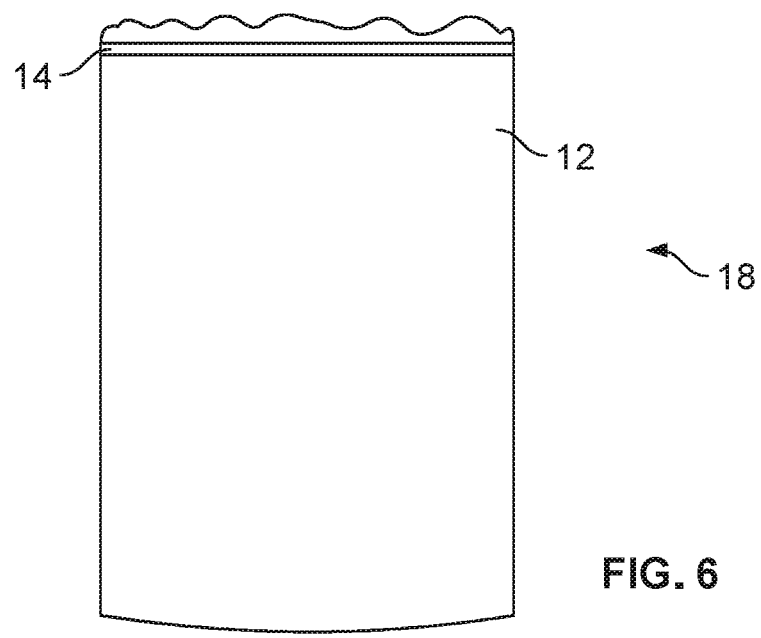
FIG. 6 shows a front elevation view of the bag of FIG. 1 when torn open.
Figure 7:
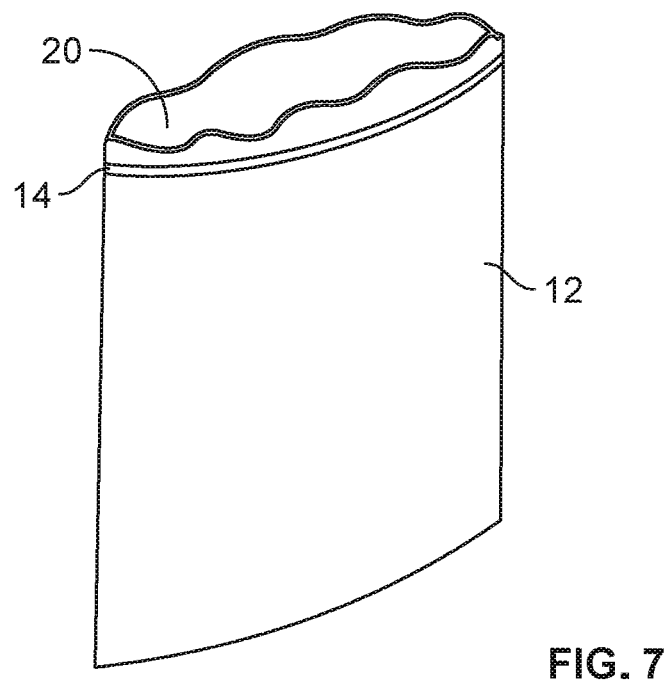
FIG. 7 shows a front perspective view of the bag of FIG. 1 when torn open.
Figure 8:
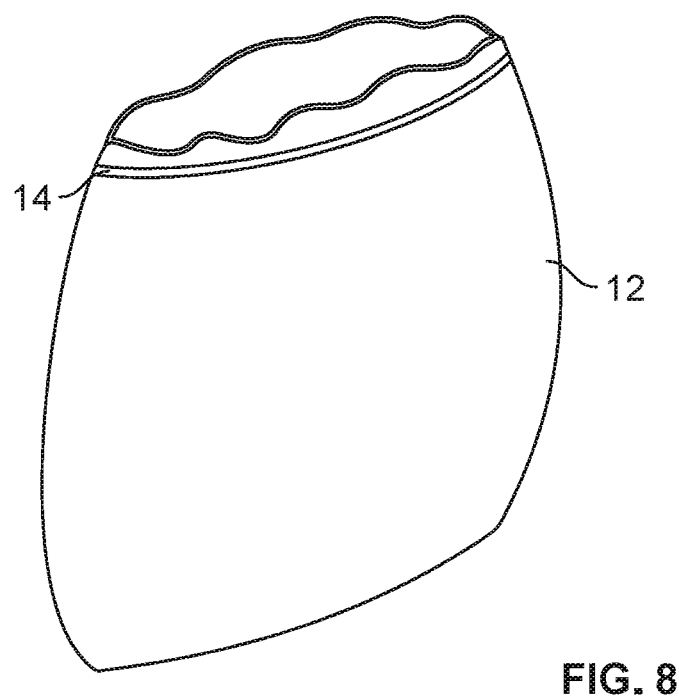
FIG. 8 illustrates a bag having a used wipe and a used condom when not resealed.
Figure 9:
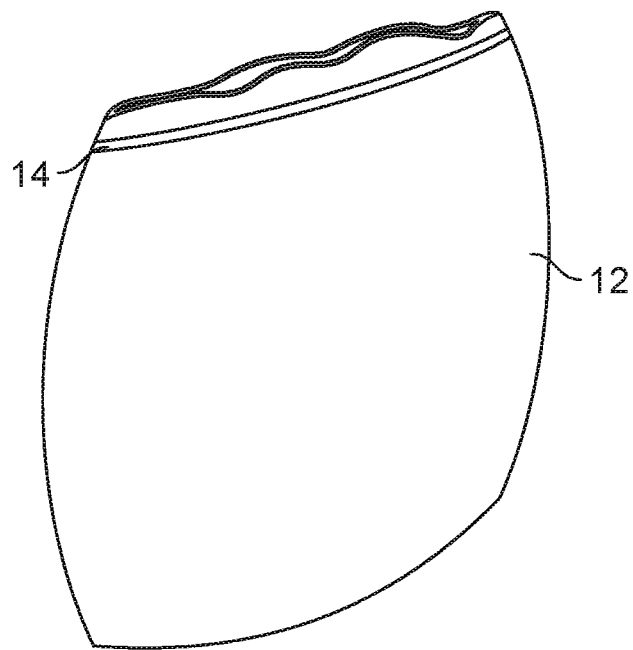
FIG. 9 illustrates a bag having a used wipe and a used condom when resealed.
Figure 10A:
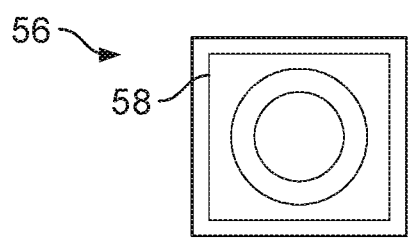
FIG. 10A illustrates a condom contained in an unopened condom wrapper.
Figure 10B:
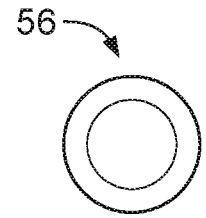
FIG. 10B illustrates an unused condom.
Figure 11:
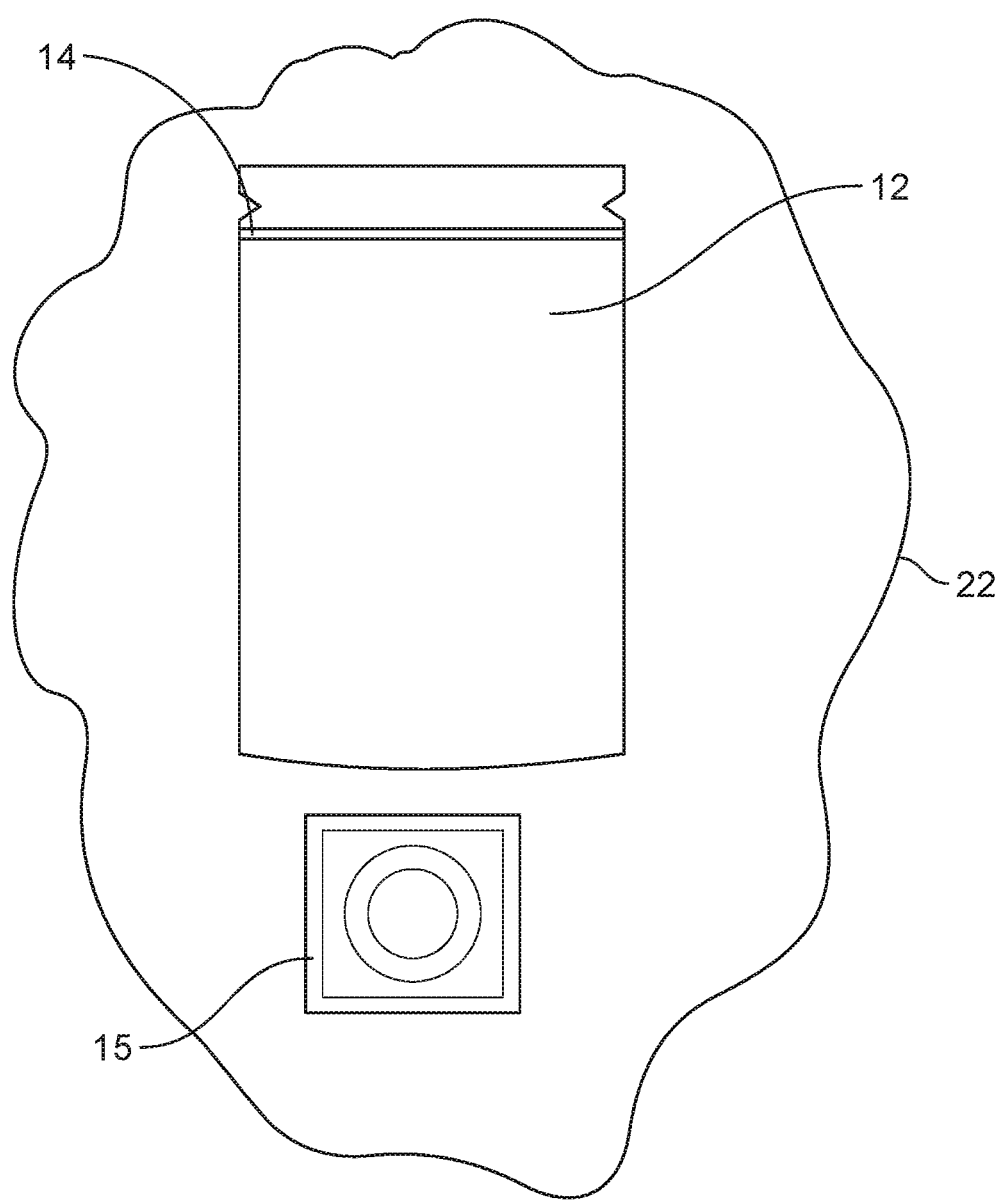
FIG. 11 illustrates the kit and the unopened condom in an outer wrap.

Referring to FIGS. 1-13, a wipe and bag kit 10 has been developed. The wipe and bag kit 10 comprises a sealed bag 12. The bag 12 may comprise a releasable seal 14. In some embodiments, the bag 12 may be resealable. For example, releasable seal 14 may also be resealable. The bag 12 may have a sealed state 16 (FIG. 1) defined by when the bag 12 is unopened and an open state 18 (FIGS. 6-8) defined by when the sealed bag 12 is opened (i.e., the seal is broken and not resealed). The bag 12 may be constructed of any suitable material, such as a polymer, aluminum, or combinations thereof, such as a metalized film. The bag 12 may be free of surface markings (such as text) so as to be discreet. The bag 12 defines an interior chamber 20. One or more of the kits 10 may be provided in an outer wrap 22 such that the kits may be conveniently shipped and sold in multiples or so that instructions for use or other markings (such as trademarks) can be provided on the outer wrap 22 rather than the bag 12. The bag 12 may include an opener element 24, such as a perforation or notch 26 for easily opening (e.g., tearing open) the bag open.

When the bag 12 is in the sealed state 16, the interior chamber 20 contains one or more wipes 28. In some embodiments, the one or more wipes 28 may be at least one wipe, at least two wipes, at least three wipes, at least five wipes, at least ten wipes, or at least twenty wipes. In other embodiments, the one or more wipes 28 is a single wipe. Embodiments containing a single wipe 28 may be particularly advantageous such that wipe and bag kit is single-use and disposable. The one or more wipes comprise a flexible body 30. The flexible body 30 may be constructed of any suitable material, such as one or more fabrics and/or papers. In some embodiments, the flexible body 30 may be constructed of fibers such as one or more of cotton, rayon, polyester, polyethylene, and polypropylene. The flexible body 30 may be woven or non-woven. The flexible body 30 may be constructed of one or more layers, such as one layer, two layers, three layers, four layers, or five or more layers. In some embodiments, the flexible body 30 may be constructed such that the wipe 28 is flushable in a toilet and meets applicable standards to be flushed according to plumbing rules and regulations. The wipe 28 may be safe to be flushed in household plumbing systems that use a septic system.

Figure 4:
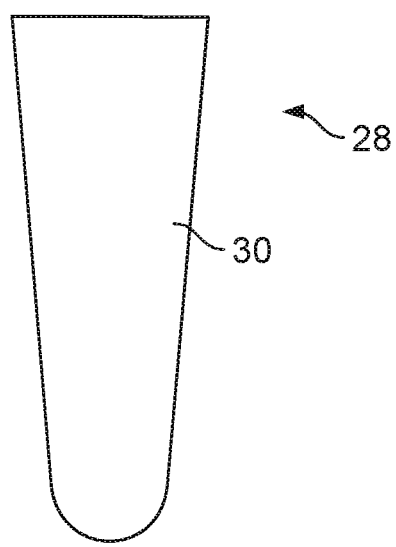
FIG. 4 shows a front elevation view of another embodiment of a wipe.
Figure 5:
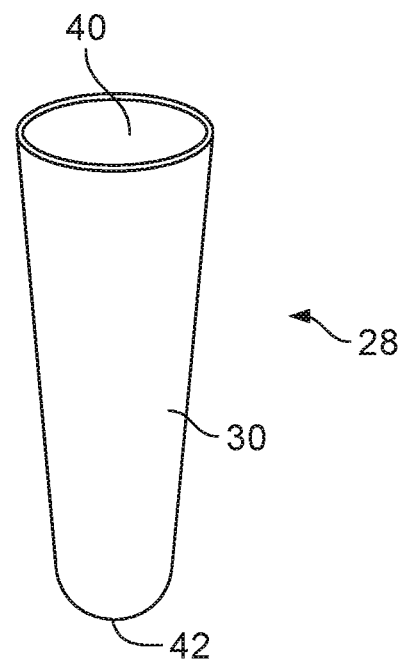
FIG. 5 shows a front perspective view of the wipe of FIG. 4.

The flexible body 30 may be formed in any suitable manner. In some embodiments, the flexible body 30 is integrally formed (FIGS. 4 and 5). In some embodiments, the flexible body 30 may be formed by using a sheet of fabric 32, folding the sheet of fabric 32 on itself lengthwise to create a bottom fold 34, and fastening side edges 36 with a fastener 38, such as an adhesive, stitching, a heat seal or any other suitable fastener. When a heat seal is used as fastener 38, the heat seal may be formed by melting, or partially melting, one or more polymers of which the flexibly body is constructed, whether completely or partially. Examples of the one or more polymers suitable for heat sealing include one or more of polyethylene, polyamide, polyester, polypropylene, polycarbonate, and polystyrene.

The flexible body 30 may have any suitable profile to cooperatively receive a human male penis. In some embodiments, the flexible body 30 has a rectangular profile when not worn (FIGS. 2 and 3) such that when the flexible body 30 is worn, the body generally contours around the penis. In other embodiments, the flexible body 30 may be generally cylindrical in shape so as to be complementary in shape to the human penis, either erect or flaccid (FIGS. 4 and 5).

The flexible body 30 may comprise an open end 40 and a closed end 42. The flexible body 30 may be shaped complementary to a human penis (either erect or flaccid) such that the flexible body 30 may cooperatively receive, at least partially, the human penis through the open end 40 and toward the closed end 42. The flexible body 30 may taper generally inwardly from the open end 40 toward the closed end 42. The flexible body 30 may comprise an extension portion 44 where the fabric body extends outwardly from the open end 40 to enable the wipe to be more easily positioned and worn.

Figure 12:
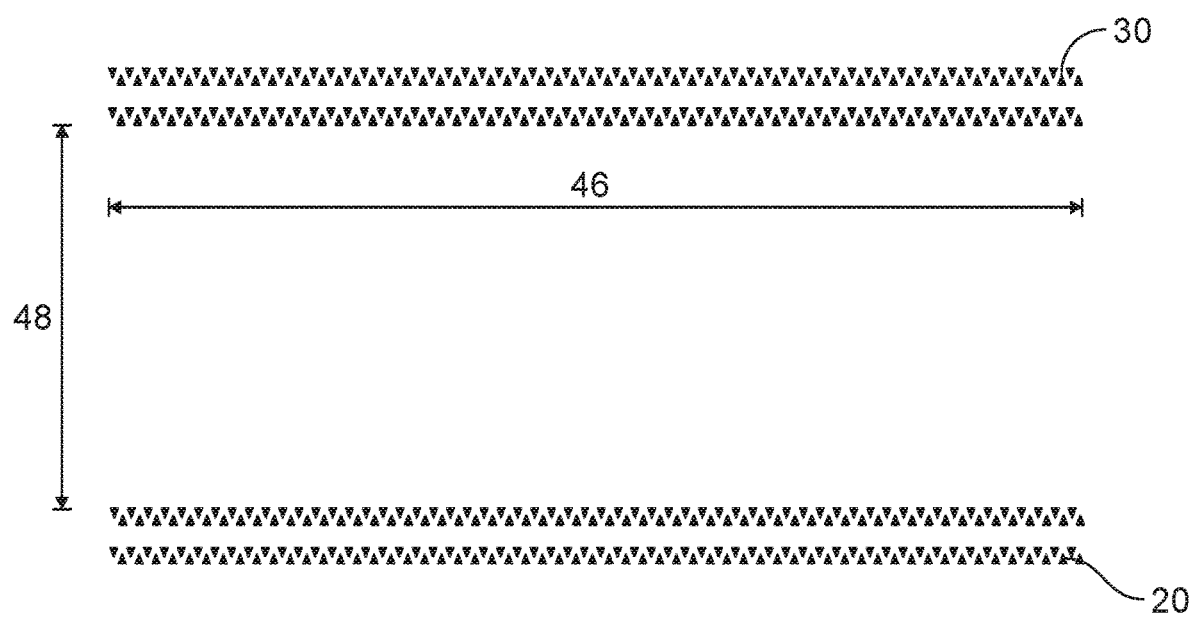
FIG. 12 illustrates the construction of a fabric body.

As it can be appreciated that penis shapes and sizes differ between human males, the size and shape of the flexible body 30 may be correspondingly varied so as to cooperatively receive penises from different individuals. In some embodiments, the flexible body 30 may be provided in one or more sizes (e.g., large & extra large) or provided in one or more different shapes (e.g., more or less tapered or for a "mushroom-shaped" penis glans). Referring to FIG. 12, by way of example, the flexible body 30 may have a length 46 of between 50 mm and 500 mm, between 100 mm and 250 mm, between 150 mm and 200 mm, or about 178 mm. the flexible body may have a width 48 of between 25 mm and 400 mm, between 50 mm and 300 mm, between 75 mm and 200 mm, between 100 mm and 150 mm, or about 114 mm.

Figure 13:
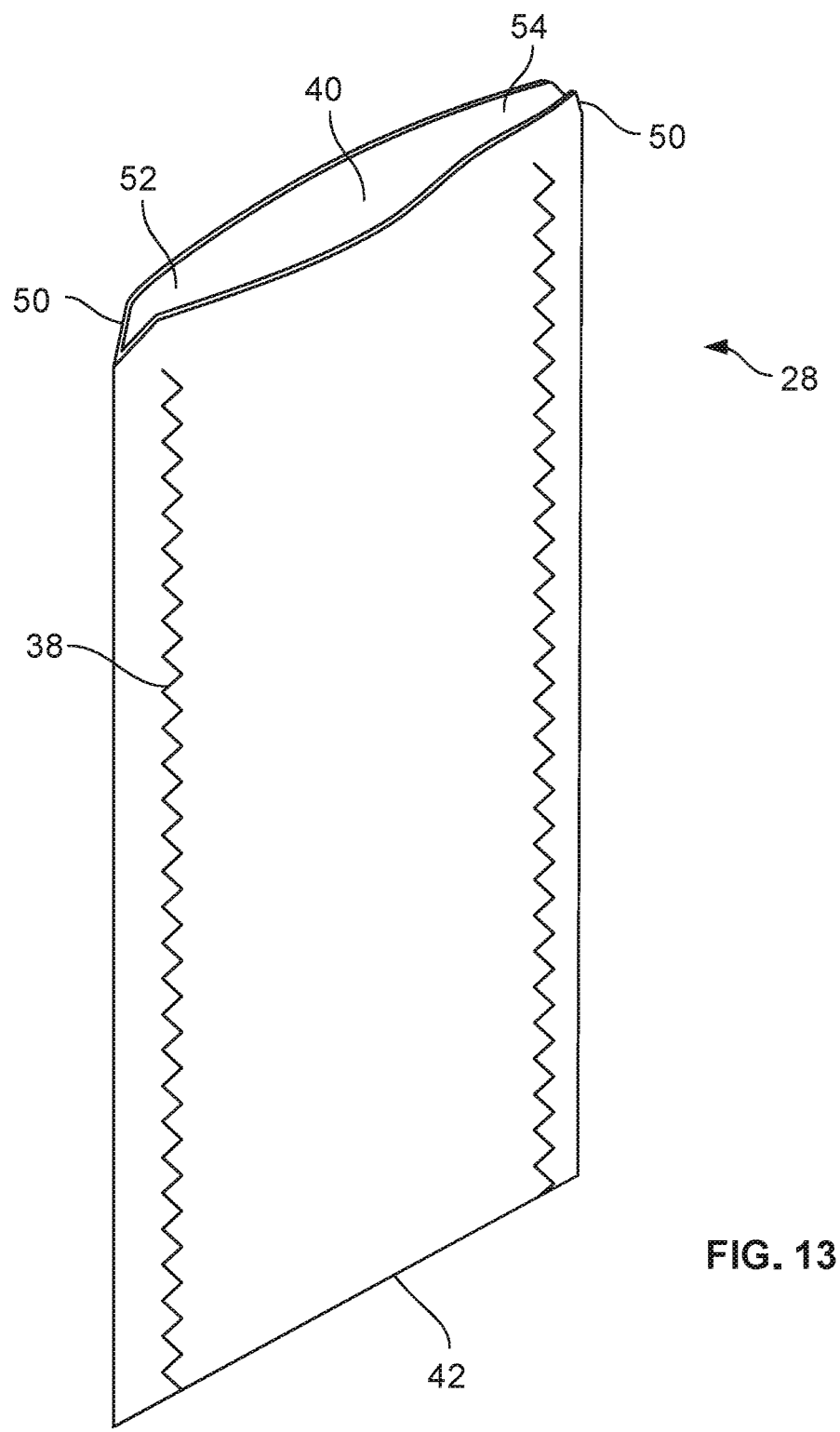
FIG. 13 illustrates a front perspective view of a wipe having open corners.

Referring to FIG. 13, the flexible body 30 may comprise one or more open corners 50, which may also be described as slits, disposed at the open end 40 of the flexible body 30. The one or more open corners 50 are beneficial, as they allow open end 40 to freely expand to assist in positioning and inserting his penis into the body 20. In some embodiments, the open corners 50 comprise a first open corner 52 and a second open corner 54 disposed oppositely around the open end 40 from the first open corner 52.

In some embodiments, the kit 10 may include a condom 56. The condom may be wrapped in the outer wrap 22. The condom 56 may itself be contained in a condom wrapper 58. When the condom 56 is provided with the kit 10, the kit 10 provides a convenient condom and condom-disposal means (i.e., the bag 12), as well as a penis clean-up means (i.e., the wipe 28).

The wipe 28 may comprise a composition, such as an aqueous or alcohol-based composition. The wipe 28 may be pre-soaked (i.e., pre-wetted, impregnated, or saturated) in the composition. The wipe 28 may comprise, for example, at least 5% by weight, at least 10% by weight, at least 25% by weight, at least 50% by weight, or at least 75% by weight the composition. The composition may comprise water in an amount of at least 10%, at least 25%, at least 50%, at least 75%, at least 90%, at least 95%, at least 97%, at least 98%, or at least 99% by weight.

The wipe 28, whether directly or as part of the composition, may comprise one or more additives, such as a preservative. Any suitable preservative may be included. Examples of preservatives that may be used include methylisothiazolinone, sodium benzoate, phenoxyethanol, potassium sorbate, grapefruit seed extract, or silver dihydrogen. When included as part of the composition, the composition may comprise 0.001% to 2% or 0.1% to 1% of the preservative by weight.

The one or more additives may include a lubricant to enable the wipe 28 to more easily slide across the penis. Any suitable lubricant may be included. Examples of lubricants that may be used include butoxy PEG-4 PG-amodimethicone, dimethicone, or a water-based lubricant.

The one or more additives may include at least one skin softener or skin conditioner, such as caprylyl glycol. The one or more additives may include at least one skin cleanser, such as coco-betaine. The one or more additives may include at least one buffer, such as citric acid, malic acid, sodium citrate, sodium bicarbonate, or sodium phosphate. The one or more additives may include at least one emulsifier, such as polysorbate 20, xanthan gum, guar gum, or propylene glycol alginate. The one or more additives may include at least one whitener, such as sodium citrate. The one or more additives may include a thickener, such as xanthan gum or behenyl alcohol. The one or more additives may include at least one phytoextract, such as aloe vera (*Aloe barbadensis* leaf extract) or *matricaria* (*Chamomilla recutita* flower extract), green tea (*Camellia sinesis* leaf extract), coconut (*Cocos nucifera*) oil, shea tree (*Vitellaria paradoxa*) butter, or cucumber (*Cucumis Sativus* fruit extract). The one or more additives may include vitamin E (natural and synthetic tocopheryl acetate), glycerin. The one or more additives may include at least one fragrance.

In some embodiments, the wipe 28 is hypoallergenic, such as latex-free. The wipe 28 may be free of any of the additives discussed herein (e.g., free of fragrances). The wipe 28 may be provided with the bag 14 and/or the condom 56, such as part of the kit 10, or independently thereof.

Methods of using the kit 10 and the wipe 28 are disclosed. Beneficially, the wipe 12 can be used in methods for cleaning a human penis wearing a condom (which may or may not be condom 56) and in methods for removing a condom from a human penis. The method includes providing the wipe 28 and inserting the human penis wearing a condom through the open end 40 of the wipe 28 such that the penis is at least partially within the wipe 28 such that the wipe 28 covers at least a portion of the penis and the condom. The method includes removing the wipe 28 and the condom together from the penis. The wipe 28 and the condom may be removed together by, for example, exerting pressure around the open end 40 of the wipe 28 on the penis (and thereby also around the condom) and pulling the wipe 28 and the condom together from the penis. The wipe 28, especially in embodiments in which the wipe 28 is pre-wetted, cleans the penis of ejaculate or other fluids that may be present on while providing a barrier so that the person performing the removing step (who may or may not be the wearer of the condom) of the wipe 28 need not directly touch the condom, thereby avoiding any bodily fluid on the external surface of the condom. Beneficially, in this way, the wipe 28 aids in the removal of the condom and cleans the penis simultaneously.

In aspects of the disclosure having the bag and wipe kit 10, the kit 10 is particularly advantageous as the bag 14 provides a container for shipping, selling, and storing the wipe 28 before the wipe 28 is used and a container within which to discard the removed and used wipe 28 (within the interior chamber 20) and condom. Methods of cleaning of the penis or removing the condom may include opening the sealed bag 14 from the sealed state 16 to the open state 18, followed by removing the wipe 28 from the bag 14, before the inserting of the penis into the open end 40 of the wipe 28. The methods may include, after removing the wipe 28 and the condom, placing the removed wipe 28 and the removed condom within the interior chamber 20 of the bag 14. In embodiments of the bag 14 where the bag 14 is resealable, the bag 14 may be resealed after the used wipe 18 and used condom are placed within the interior chamber 20. The bag 14 may be dimensioned to completely receive the removed wipe 28 and the removed condom. The bag 14 may then be disposed, such as with household trash.

Although embodiments of the disclosure have been described using specific terms, devices, and methods, such description is for illustrative purposes only. The words are words of description rather than of limitation. It is to be understood that changes and variations may be made by those of ordinary skill in the art without departing from the spirit or scope of the present disclosure, which is set forth in the following claims. It is further noted that any range provided herein provides support and a basis for any subset within that range. Further embodiments of the disclosure contain combinations, or exclusions, of different embodiments described herein.

Thus, although there have been described embodiments of the present invention of a new and useful wipe and wipe and bag kit, and it is not intended that such references be construed as limitations upon the scope of this invention except as set forth in the following claims.

What is claimed is:

1. A method of cleaning a human penis wearing a condom, comprising:
   providing a wipe pre-wetted with a composition including water, the wipe including an open end, wherein the wipe is shaped to cooperatively receive the human penis wearing the condom through the open end, and wherein the wipe is provided in a bag in a sealed state;
   opening the bag from the sealed state to an open state;
   removing the wipe from the bag in the open state;
   inserting the human penis through the open end at least partially within the wipe; and
   removing the wipe and the condom together from the penis.

2. The method of claim 1, further comprising:
   after the removing, placing the removed wipe and the removed condom within the bag in the open state.

3. The method of claim 2, wherein the bag comprises a resealable seal.

4. The method of claim 3, further comprising resealing the bag having the removed wipe and removed condom from the open state to a closed state.

5. The method of claim 4, further comprising disposing of the resealed bag having the removed wipe and removed condom.

6. The method of claim 1, wherein the wipe is constructed of a fabric.

7. The method of claim 1, wherein the wipe is constructed of a multi-layer flexible body.

8. The method of claim 1, wherein the wipe comprises a cleaning agent.

9. The method of claim 1, wherein the wipe comprises one or more open corners at the open end.

10. The method of claim 9, wherein the one or more open corners comprise a first open corner and a second open corner disposed oppositely around the open end from the first open corner.

11. The method of claim 1, wherein the wipe further comprises an additive selected from the group consisting of: a preservative, a lubricant, a cleaner, a fragrance, an emulsifier, a whitener, a skin softener, aloe, vitamin E, and combinations thereof.

12. The method of claim 1, wherein the composition comprises at least 90% water by weight.

13. The method of claim 12, wherein the composition comprises one or more of a preservative, a lubricant, a cleaner, a fragrance, an emulsifier, a whitener, a skin softener, aloe, vitamin E, and combinations thereof.

14. The method of claim 1, wherein the wipe is latex-free.

15. The method of claim 1, further comprising providing a condom and inserting the human penis in the condom.

16. The method of claim 15, wherein the provided condom and provided wipe are removed from an outer wrap.

17. The method of claim 1, wherein the wipe is hypoallergenic.

18. The method of claim 1, wherein the removing of the wipe and the condom together from the penis comprises exerting pressure around the open end of the wipe on the penis and the condom and pulling the wipe and the condom together from the penis.

19. A method of cleaning a human penis wearing a condom, comprising:

providing a flexible wipe in a bag in a sealed state, the wipe pre-wetted with a composition including at least 25% water by weight of the composition and one or more of a preservative, a lubricant, a skin cleanser, a fragrance, an emulsifier, a skin softener, aloe, vitamin E, and combinations thereof, wherein the wipe includes an open end, and wherein the wipe is shaped to cooperatively receive the human penis wearing the condom through the open end;

opening the bag from the sealed state to an open state;

removing the wipe from the bag in the open state;

inserting the human penis through the open end at least partially within the wipe; and removing the wipe and the condom together from the penis.

20. The method of claim 19, further comprising:

after the removing, placing the removed wipe and the removed condom within the bag in the open state.

21. The method of claim 20, wherein the bag comprises a resealable seal.

22. The method of claim 21, further comprising resealing the bag having the removed wipe and removed condom from the open state to a closed state.

* * * * *